United States Patent [19]

Wolf

[11] Patent Number: 4,928,917
[45] Date of Patent: May 29, 1990

[54] HOLDING FIXTURE, IN PARTICULAR FOR MEDICAL USE

[76] Inventor: Hans-Joachim Wolf, Theodor-Schweitzer-Str. 1, D-7137, Sternenfels-1, Fed. Rep. of Germany

[21] Appl. No.: 173,475

[22] Filed: Mar. 25, 1988

[30] Foreign Application Priority Data

Mar. 26, 1987 [DE] Fed. Rep. of Germany ....... 3710016

[51] Int. Cl.⁵ .............................................. B65D 45/00
[52] U.S. Cl. ..................................... 248/507; 248/508; 206/363; 206/370; 206/563; 422/297; 422/300; 422/310
[58] Field of Search ............................. 211/60.1, 70.6; 312/209, 111; 206/363, 365, 368, 370, 438, 493, 560; 422/297, 300, 310; 248/507, 508, 73

[56] References Cited

U.S. PATENT DOCUMENTS

| 893,754 | 7/1908 | Russel | 248/507 |
| 3,575,373 | 4/1971 | Reinhardt | 248/509 |
| 4,043,754 | 8/1977 | Sklar | 21/82 |
| 4,135,868 | 1/1979 | Schainholz | 422/310 |

FOREIGN PATENT DOCUMENTS 2713094 10/1978 Fed. Rep. of Germany .

Primary Examiner—Christine M. Nucker
Assistant Examiner—Gregory R. Muir
Attorney, Agent, or Firm—Spensley Horn Jubas & Lubitz

[57] ABSTRACT

A holding fixture for medical use, serving to support and fix articles, such as medical instruments, that are to be sterilized, and intended for mounting on a support panel, composed substantially of two parts: a retaining post, provided at least in part with profiling, that is to be locked into place on the support panel, and a bracket that can be slipped onto this retaining post, the mounting aperture of the bracket being such that it is lockable by positive engagement with the retaining post. By this principle, the most varied kinds of holding fixtures, adapted individually to the position and shape of each instrument, can be devised with a minimum number of different components. These brackets can easily be locked in place and released again by exerting pressure and tension upon corresponding regions of the brackets, making them extremely simple to use.

12 Claims, 4 Drawing Sheets

HOLDING FIXTURE, IN PARTICULAR FOR MEDICAL USE

BACKGROUND OF THE INVENTION

The present invention relates to a holding fixture, in particular for medical use, for supporting and fixing articles, for example a set of surgical instruments, to be sterilized. The holding fixture is constructed to be inserted into a support panel, which to this end has a large number of insertion apertures for a plurality of such holding fixtures for different articles.

Such holding fixtures are disclosed in U.S. Pat. No. 4,135,868, issued to Herbert Schainholz on Jan. 23, 1979. The device disclosed in that patent includes a perforated support panel set into a suitcase-like receptacle, and instrument support bases which can be inserted into apertures in the support insert and locked in place. The instrument support bases in turn receive comblike support or bridge members onto or into which surgical instruments, for example, can be placed. For positionally correct fixation of such instruments, the known device provides similar holding fixtures set into a second support panel that is fitted into the lid of this suitcase-like receptacle. However, instead of the bridge-like support members, these holding fixtures have elastic parts, for example foam blocks, such that when the lid of the receptacle is closed, these elastic parts fix the instrument parts that are to be retained on their support bases.

It will be readily apparent that the instruments will be fixed in place only when the instrument receptacle is closed. When the receptacle is open, the instruments are no longer positively held in place and can fall out if the receptacle is tilted or jarred. In other words, what is provided is a kind of "collective" securing of the articles to be sterilized in their positions on the support panel when the receptacle is closed.

The holding fixtures disclosed in the cited patent have only limitedly suitability for medical instruments, such as endoscopes, that are complicated in shape, for example comprising various parts of differing diameters and differing in shape from one another.

Relatively short annular elements of large diameter, for example, cannot be satisfactorily fixed with these known holding fixtures.

SUMMARY OF THE INVENTION

It is accordingly an object of the present invention to provide holding fixtures that are suitable for holding instruments having a wide variety of shapes.

Another object of the invention is to provide fixtures which can positively retain each instrument or part individually.

The above and other objects are achieved, according to the present invention, by a holding fixture mountable in an insertion opening provided in a support panel which has a plurality of insertion openings for receiving a plurality of such holding fixtures, the fixture serving for supporting and securing an article and the fixture comprising: at least one retaining member having an at least partially profiled outer surface; and at least one resiliently deformable bracket member having an aperture dimensioned to permit passage of the retaining member therethrough, when the bracket member has a first selected orientation relative to the retaining member, and to establish locking engagement between the bracket member, in the region of the edge of the aperture, and the retaining member, accompanied by elastic deformation of the bracket member, when the bracket member has a second selected orientation relative to the retaining member.

In contrast to the holding fixtures disclosed in U.S. Pat. No. 4,135,868, the holding fixtures according to the present invention enable individual retention and fixation of instruments or instrument parts. In particular, an adaptation to the thickness or height of a particular part is attainable simply by pressing an associated retaining bracket, or member, down to an appropriate level along the retaining post.

According to preferred embodiments of the invention, the retaining post is constituted by a cylindrical molded part on the circumference of which a plurality of detent ribs, located one above the other, is provided and the brackets are made of a resilient plastic material and have a rectangular cross section.

In this embodiment, simple manufacture of both parts forming the holding fixture according to the invention is assured, and by simple variations of the brackets and by combining such parts on one or two retaining posts, a large number of holding fixture configurations can be attained with a minimum number of basic components. The cooperation according to the invention of the retaining post and brackets, that is their elastic locking in an arbitrarily selected positions in terms of height, therefore makes it possible to retain arbitrarily shaped or composed medical instruments at the necessary locations for this purpose on the support panel, and optimal use of the surface area of the support panel can be made, since the holding fixtures themselves occupy only a minimum of space.

A particularly important feature of the invention is the extreme ease of use of these holding fixtures; also, locking and unlocking of the holding fixture for fixation of an article, e.g. a medical instrument or instrument, can be accomplished with a single motion of the hand, substantially by pressing a finger against an appropriate point of the bracket.

Further features of the invention will be described below.

Several exemplary embodiments of holding fixtures according to the invention will now be described in further detail, referring to the drawings.

DESCRIPTION OF THE PREFERRED EMBODIMENTS

The principle of the holding fixture according to the invention will now be described in detail, with initial reference being made to FIGS. 1 and 2.

Figure 1:
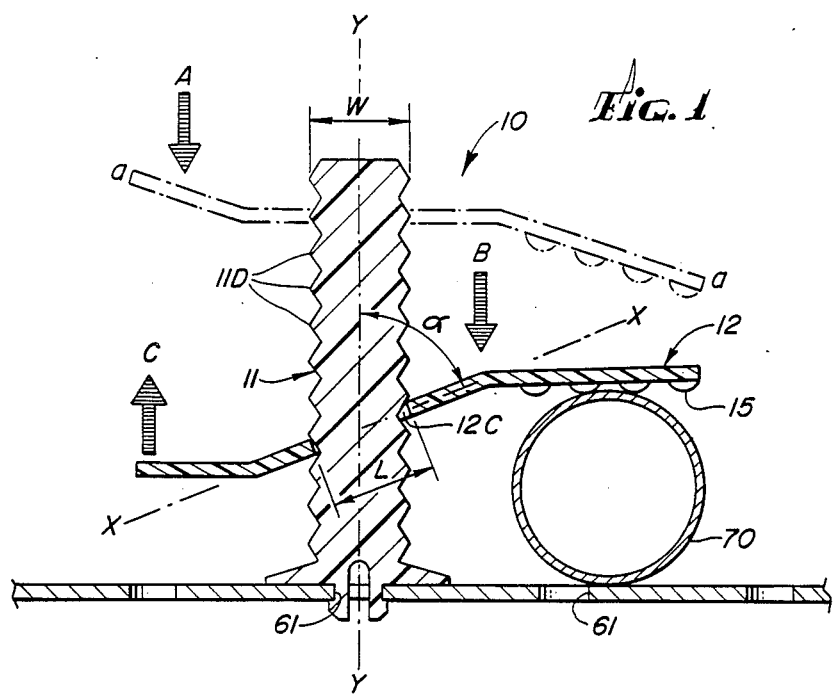
FIG. 1 is a cross-sectional elevational view of one preferred embodiment of a holding fixture according to the invention, mounted on a support panel, in the plane I—I of FIG. 2.
Figure 2:
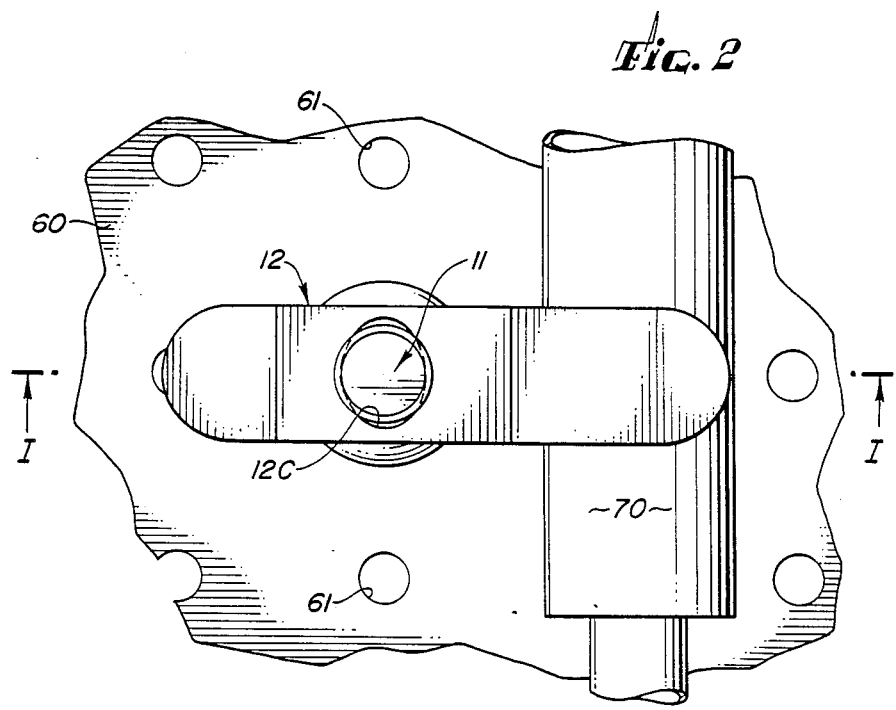
FIG. 2 is a plan view of the inserted holding fixture of FIG. 1.

In the exemplary embodiment of FIGS. 1 and 2, one holding fixture 10 according to the invention consists of only two parts, namely a retaining post 11 and a hold-down bracket 12.

The retaining post 11 is constituted by a cylindrical molded part which is lockable via a detent part of post 11 in position in any selected one of an array of apertures 61 formed in a support panel 60. To this end, the base portion of the retaining post 11, which base portion forms the detent part, is slit along its longitudinal axis Y—Y, so that the two facing parts of the base portion, which are separated by the slit, are resiliently compressed upon insertion into aperture 61, and spread apart resiliently again after passing through the aperture, whereupon detent shoulders of the base portion then grip the support panel 60 from below. This type of anchoring of the holding fixtures corresponds substantially to the technique described in U.S. Pat. No. 4,135,868, and so need not be described in detail here.

For stabilizing retaining post 11 in its vertical position on support panel 60, its base portion is provided with a radially enlarged conical part that is pressed against the upper surface of support panel 60.

On its circumference, cylindrical retaining post 11 has ribs 11D which extend parallel to one another around the entire circumference of post 11 to serve as abutments for bracket 12, as will be explained in further detail below.

Bracket 12 is a resiliently deformable plastic part having a middle portion in which an aperture 12C is formed and two end portions which are slightly bent at an angle to the middle portion. One end portion serves to retain a medical instrument, or instrument part, 70 in place and the other end portion is provided for moving the bracket.

The dimensioning of aperture 12c in relation to the cross section of retaining post 11 is of particular importance. The inside dimension L of aperture 12C in the plane X—X of the middle portion and along plane I—I (the longitudinal plane of the bracket 12) must be made larger than the largest diameter W of retaining post 11, measured perpendicular to axis Y—Y, on the one hand, in order to enable simple fitting of bracket 12 onto retaining post 11, and must be made only slightly larger than the largest diameter W, on the other hand, to enable secure locking of bracket 12 in place on post 11.

This permits bracket 12 to be moved freely along retaining post 11 whenever the plane X—X of aperture 12C is substantially perpendicular to the longitudinal axis Y—Y of retaining post 11, because in that case there is still sufficient play to both sides of the ribs 11D for a vertical motion of bracket 12. However, if the middle portion of bracket 12 is tilted with respect to the longitudinal axis Y—Y of retaining post 11, that is, when the angle a, shown in FIG. 1, is decreased from 90°, a position is attained at which the projection of the inside dimension L into a plane perpendicular to axis Y—Y becomes smaller than the largest diameter W of retaining post 11, so that a clamping or detent effect arises which, under the influence of the resiliency of the plastic material, has the effect of fixing bracket 12 on retaining post 11, one of the profile ribs 11D then serving as an abutment for a circumferential edge of aperture 12C.

Based on these principles, the holding fixture shown in FIGS. 1 and 2 is used in the following manner:

For locking a medical instrument 70, first bracket 12 is placed in a position upon retaining post 11, as indicated by the broken line a—a. Since the middle portion of bracket 12 is then perpendicular to longitudinal axis Y—Y, bracket 12 can consequently slip downward until the underside of bracket 12, which is provided with instrument retaining bosses 15, rests on the instrument 70 (this position is not shown).

If the person using the equipment then presses in the direction of the arrow A upon the end portion of bracket 12 which is opposite the end portion carrying bosses 15, then bracket 12 moves farther downward so that the middle portion containing aperture 12C undergoes further tilting in the direction to reduce the magnitude of angle a and at the same time the pressure upon the instrument 70 that is to be secured is increased.

Finally, the terminal position of bracket 12, shown in solid lines in FIG. 1, is attained, at which the angle a between the plane X—X of aperture 12C and the longitudinal axis Y—Y of retaining post 11 assumes a certain value, and locking occurs. By correspondingly varying the locking force in the direction of arrow A, two or three different detent positions on detent ribs 11D can be attained as a rule, which, because of the resiliency of the plastic material of bracket 12, can cause a more or less strong retaining pressure to be effected upon the instrument 70 to be secured.

In order to subsequently withdraw bracket 12, it is generally necessary to return the plane X—X of the middle portion of bracket 12 to an orientation which is substantially perpendicular to the longitudinal axis Y—Y, which can for example be done by pressing in the direction of the arrow B, optionally while simultaneously pulling in the direction of the arrow C, so that then bracket 12 is moved back into the position a—a shown in dashed lines, and can be removed from retaining post 11 as desired. Alternatively to that option, it is also conceivable to provide the retaining post 11 with an elastic or, in other words, pivotable base portion, so that retaining post 11 can be tilted, or inclined, toward the left in FIG. 1 to bring the plane X—X into a position which is perpendicular to the longitudinal axis Y—Y, which as described above is a precondition for releasing the locking.

FIGS. 3–6 show further exemplary embodiments, which by utilizing the above-described principle make it possible to accomplish an arbitrary, individual retention of the most varied kinds of articles using differently shaped brackets and support parts.

Figure 3:
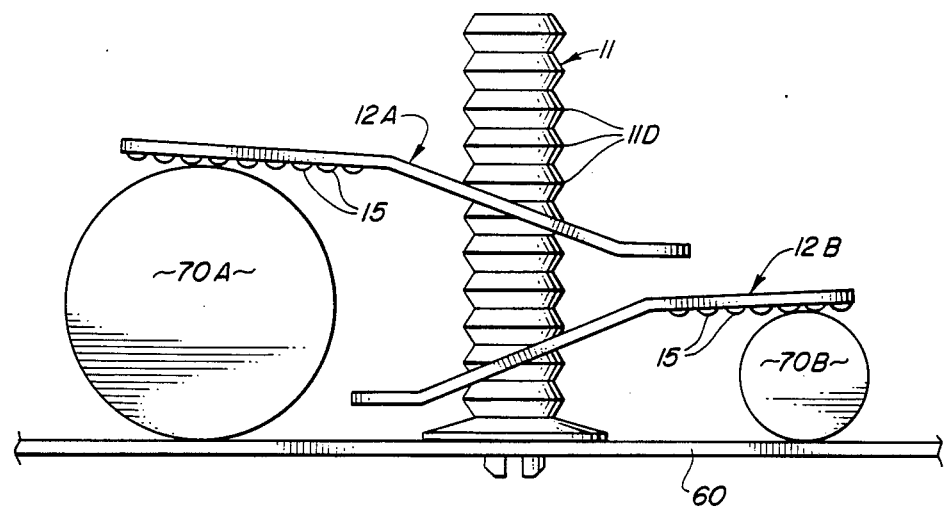
FIG. 3 is a side elevational view of another holding fixture arrangement according to the invention.

FIG. 3, for example, shows the use of two hold-down brackets 12A and 12B on a common retaining post 11 for the retention of articles or instruments 70A and 70B having different diameters. It is readily apparent that the angular positions of the two brackets 12a and 12b relative to one another about the longitudinal axis of post 11 is also variable over a wide range.

Figure 4:
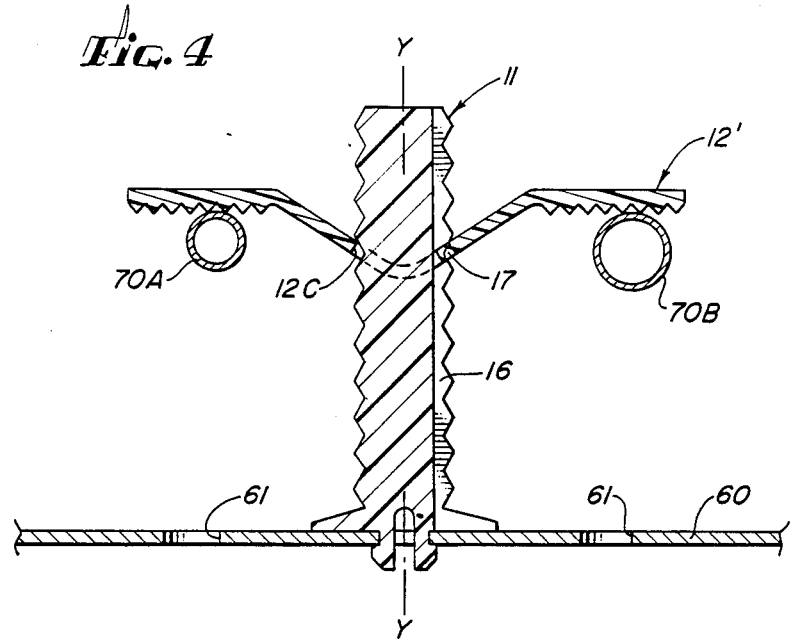
FIG. 4 is an elevational cross-sectional view, in the plane IV—IV of FIG. 5, of an embodiment of a holding fixture according to the invention having a symmetrical bracket.
Figure 5:
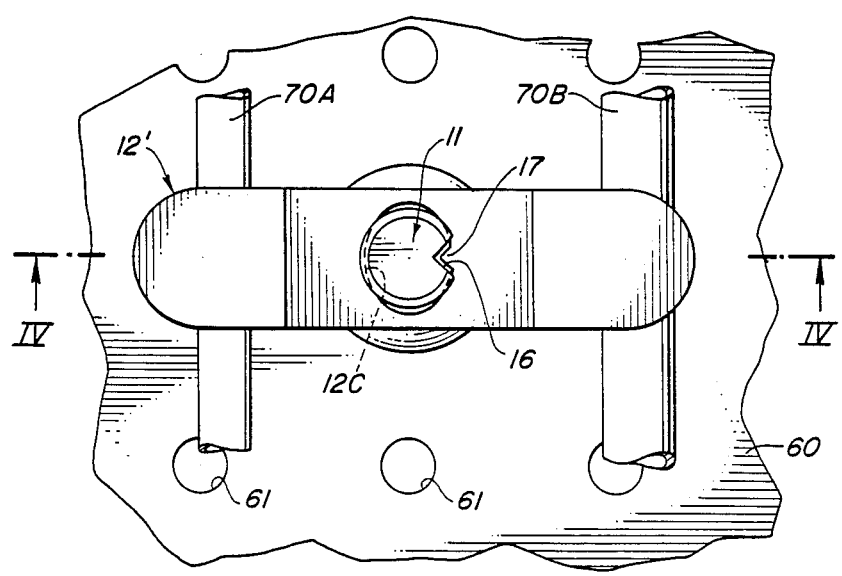
FIG. 5 is a plan view of the holding fixture of FIG. 4.

In the exemplary embodiment of FIGS. 4 and 5, the hold-down bracket 12' has a bilaterally symmetrical form so that the aperture 12C is located in the middle portion which has a V-shaped form. Additionally, in this exemplary embodiment the retaining post 11 has a vertical longitudinal groove 16, which is engaged by a guide lug 17 of bracket 12'. Thus a certain directional orientation of bracket 12' relative to support panel 60 can be specified, if the type and shape of the instruments 70A and 70B that are to be retained makes this appear suitable. Bracket 12' can be released by pushing upward on the middle portion, preferably at points directly adjacent post 11, possibly while simultaneously pushing downward on one or both end portions. In view of the flexibility of bracket 12', this will enable the middle portion to be deformed sufficiently to effect bracket release. Alternatively, release could be effected by pulling the end portions of bracket 12' away from one another while sliding the bracket up along post 11.

Figure 6:
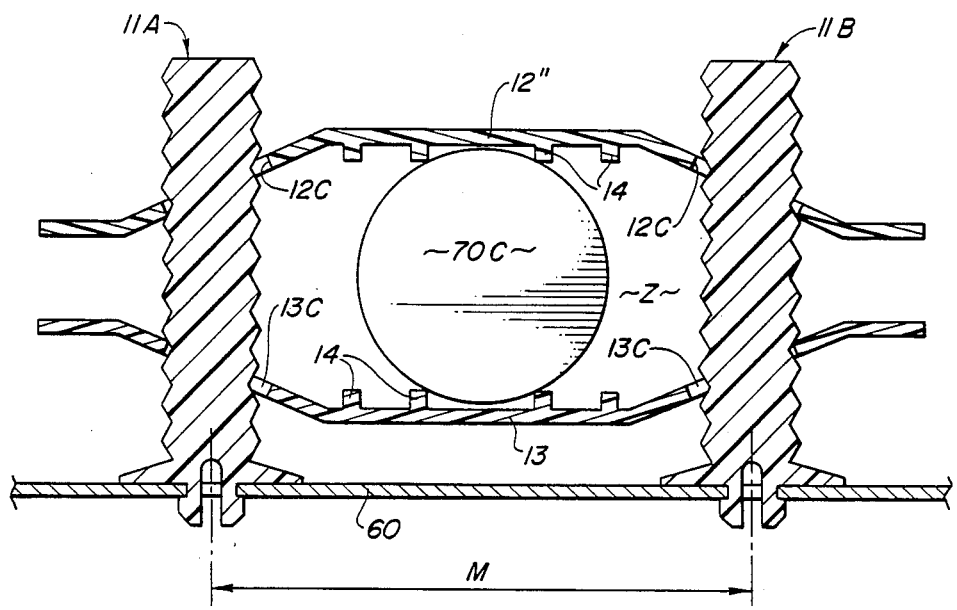
FIG. 6 is an elevational cross-sectional view of an embodiment of a holding fixture, formed of two retaining posts and two brackets each slipped onto both retaining posts.

In the exemplary embodiment of FIG. 6, finally, it is shown that two retaining posts 11A and 11B can each be connected to a bridge-like support bracket 13 and a bridge-like hold-down bracket 12", so that an instrument 70C is securely retained in the space Z between the brackets 12" and 13. Each of brackets 12" and 13 is provided with a plurality of studs 14 for retaining instrument 70C in place. Since there is a regular spacing M between apertures 61, which are distributed in a grid-like manner across support panel 60, such a variant is likewise possible at arbitrarily selected locations of support panel 60.

Bracket 12" can be removed from posts 11A and 11B by lifting up simultaneously on both end portions of that bracket. Then, after instrument 70C has been removed, bracket 13 can be removed, if desired, by lifting up on the central bridge portion thereof.

From the exemplary embodiments described, it is apparent that the modular arrangement of a plurality of retaining posts 11 and suitable hold-down and/or bearing brackets on the support panel 60 makes it possible to fix any conceivable articles securely, regardless of the particular positioning in space and regardless of the dimensions of the articles to be retained.

As is further apparent from the drawing, ribs 11D can be inclined or perpendicular to the longitudinal axis Y—Y of post 11. When ribs 11D are perpendicular to axis Y—Y, as shown in FIG. 3, a bracket 12 can be positioned more easily at any desired angular position about axis Y—Y.

The invention now being fully described, it will be apparent to one of ordinary skill in the art that many changes and modifications can be made thereto without departing from the spirit or scope of the invention as set forth herein.

What is claimed is:

1. A holding fixture mountable in an insertion opening provided in a support panel which has a plurality of insertion openings for receiving a plurality of such holding fixtures, and fixture serving for supporting and securing an article and said fixture comprising: a retaining member having an outer surface which has an at least partially ribbed profile; and a resiliently deformable bracket member detachably engageable with said retaining member and having an aperture dimensioned to permit passage of said retaining member therethrough, when said bracket member has a first selected orientation relative to said retaining member, and to establish locking engagement directly between said bracket member, in the region of the edge of said aperture, and said retaining member, accompanied by elastic deformation of said bracket member, when said bracket member has a second selected orientation relative to said retaining member.

2. A holding fixture as defined in claim 1 wherein said at least one retaining member is a cylindrical molded part having a circumferential outer surface provided with a plurality of detent ribs located one above the other and defining said at least partially profiled outer surface.

3. A holding fixture as defined in claim 1 wherein said aperture lies in a plane, said retaining member has a longitudinal axis generally parallel to said outer surface, and said aperture is slightly larger than the largest dimension of said retaining member perpendicular to said longitudinal axis of said retaining member so that the locking engagement is attained whenever said plane of said aperture is inclined with respect to said longitudinal axis of said retaining member by a predetermined angle unequal to 90°.

4. A holding fixture as defined in claim 1 wherein said bracket member is a one-piece element having two symmetrical article-retaining portions, and said aperture is centrally positioned on said bracket member between said article-retaining portions.

5. A holding fixture as defined in claim 1 wherein said bracket member has a central article-retaining portion, two of said apertures and two end regions at opposite sides of said central portion, and each said end region contains a respective one of said apertures.

6. A holding fixture as defined in claim 5 wherein said central article-retaining portion is provided with protrusions located for engaging an article and holding the article in position.

7. A holding fixture as defined in claim 1 wherein said bracket member is composed of a body of resilient plastic material having a length dimension and a rectangular cross section in a plane perpendicular to the length dimension.

8. A holding fixture as defined in claim 1 wherein said bracket member has an article-engaging portion and a support portion which contains said aperture, each of said portions is planar, and said portions are connected to one another and are inclined relative to one another.

9. A holding fixture as defined in claim 1 wherein: there are two of said retaining members each mountable in a respective insertion opening and two of said bracket members constituting, respectively, a supporting bracket for supporting an article and a hold-down bracket for holding the article in place on said supporting bracket; each said bracket member has a central article-retaining portion, two of said apertures, and two end regions at opposite sides of said central portion, and each said end region contains a respective one of said apertures; and said bracket members are mounted on said retaining members such that each aperture of each said bracket member is disposed around a respective retaining member and a space is formed between said central article-retaining portions of said bracket members for retaining the article.

10. A holding fixture as defined in claim 9 wherein each said bracket member is composed of a body of resilient plastic material having a length dimension and a rectangular cross section in a plane perpendicular to said length dimension.

11. A holding fixture as defined in claim 1 further comprising guide means having a first part formed on said retaining member and a second part formed on said bracket member for establishing a selected positional relationship therebetween.

12. A holding fixture as defined in claim 11 wherein said guide means comprise a vertical longitudinal groove in said retaining member and a guide lug on said bracket member.

* * * * *